United States Patent
Batchelor et al.

(10) Patent No.: US 11,106,818 B2
(45) Date of Patent: Aug. 31, 2021

(54) PATIENT IDENTIFICATION SYSTEMS AND METHODS

(71) Applicant: LifeMed ID, Incorporated, Citrus Heights, CA (US)

(72) Inventors: David Batchelor, Newcastle, CA (US); Catherine Schulten, North Chesterfield, VA (US); Elvar H. Olafsson, Roseville, CA (US)

(73) Assignee: LifeMed ID, Incorporated, Citrus Heights, CA (US)

( * ) Notice: Subject to any disclaimer, the term of this patent is extended or adjusted under 35 U.S.C. 154(b) by 1046 days.

(21) Appl. No.: 15/256,157

(22) Filed: Sep. 2, 2016

(65) Prior Publication Data
US 2017/0169168 A1 Jun. 15, 2017

Related U.S. Application Data

(60) Provisional application No. 62/266,277, filed on Dec. 11, 2015.

(51) Int. Cl.
*G06F 21/62* (2013.01)
*G06F 21/31* (2013.01)
(Continued)

(52) U.S. Cl.
CPC .......... *G06F 21/6245* (2013.01); *G06F 21/31* (2013.01); *G06Q 10/10* (2013.01);
(Continued)

(58) Field of Classification Search
CPC ............. G06F 21/6245; G06Q 20/206; G06Q 2220/00; H04L 63/06; H04L 63/08; H04L 67/42
(Continued)

(56) References Cited

U.S. PATENT DOCUMENTS 7,725,331 B2    5/2010  Schurenberg et al.
8,095,386 B2    1/2012  Lassetter et al.
(Continued)

FOREIGN PATENT DOCUMENTS

EP    2421217 A1    2/2012
WO    9815910 A1    4/1998
(Continued)

OTHER PUBLICATIONS

Ramesh et al., "Implementing One Time Password Based Security Mechanism for Securing Personal Health Records in Cloud," 2014 International Conference on Control, Instrumentation, Communication and Computational Technologies (ICCICCT) (Year: 2014).*
(Continued)

*Primary Examiner* — Joshua B Blanchette
(74) *Attorney, Agent, or Firm* — Fredrikson & Byron, P.A.

(57) ABSTRACT

Systems and methods for managing patient information across various electronic medical record (EMR) systems, according to some examples can involve providing a patient information management system having a cloud-based application server including a database, a client application interface and a mobile security token. A one-time verification code can be sent from the cloud-based application server to the client computing device and read using the mobile security token. The mobile security token can be matched to a patient demographic record in the database to authenticate the patient using the linked mobile security token.

25 Claims, 4 Drawing Sheets

(51) Int. Cl.
  *H04W 12/06* (2021.01)
  *G16H 10/60* (2018.01)
  *G06Q 10/10* (2012.01)
  *G06Q 20/20* (2012.01)
  *H04L 29/06* (2006.01)
  *G16H 40/20* (2018.01)
  *H04W 12/77* (2021.01)

(52) U.S. Cl.
  CPC ........... *G06Q 20/206* (2013.01); *H04L 63/06* (2013.01); *H04L 63/08* (2013.01); *H04L 67/42* (2013.01); *H04W 12/06* (2013.01); *G06Q 2220/00* (2013.01); *G16H 10/60* (2018.01); *G16H 40/20* (2018.01); *H04L 63/067* (2013.01); *H04L 63/0853* (2013.01); *H04L 63/18* (2013.01); *H04W 12/77* (2021.01)

(58) Field of Classification Search
  USPC ........................................................ 705/2, 3
  See application file for complete search history.

(56) References Cited

U.S. PATENT DOCUMENTS

| | | | |
|---|---|---|---|
| 8,973,091 | B2 | 3/2015 | Ting et al. |
| 9,092,643 | B2 * | 7/2015 | Keoh ................... G06F 21/10 |
| 9,129,046 | B2 | 9/2015 | Bess et al. |
| 9,280,684 | B1 * | 3/2016 | Kragh .................. G06F 16/245 |
| 9,378,380 | B1 * | 6/2016 | Reid ..................... G06F 21/602 |
| 9,721,118 | B2 * | 8/2017 | Heidenreich ....... H04L 63/0421 |
| 9,792,658 | B1 * | 10/2017 | Vijendra ................ G16H 10/60 |
| 2002/0029157 | A1 | 3/2002 | Marchosky |
| 2003/0037054 | A1 | 2/2003 | Dutta et al. |
| 2004/0122707 | A1 | 6/2004 | Sabol et al. |
| 2005/0125258 | A1 | 6/2005 | Yellin et al. |
| 2006/0174104 | A1 * | 8/2006 | Crichton ................ G06F 21/33 |
| | | | 713/155 |
| 2006/0229911 | A1 | 10/2006 | Gropper et al. |
| 2006/0293925 | A1 | 12/2006 | Flom |
| 2007/0016450 | A1 | 1/2007 | Bhora et al. |
| 2007/0260492 | A1 | 11/2007 | Feied et al. |
| 2008/0071577 | A1 | 3/2008 | Highley |
| 2008/0126133 | A1 | 5/2008 | Park |
| 2008/0140446 | A1 | 6/2008 | Rosenfeld et al. |
| 2009/0024416 | A1 | 1/2009 | Mclaughlin et al. |
| 2009/0240681 | A1 | 9/2009 | Saddiqi et al. |
| 2009/0265776 | A1 | 10/2009 | Baentsch et al. |
| 2010/0115591 | A1 | 5/2010 | Kane-Esrig |
| 2010/0169263 | A1 * | 7/2010 | Korpman ............... G16H 10/60 |
| | | | 706/50 |
| 2010/0219241 | A1 | 9/2010 | Corwin et al. |
| 2011/0071852 | A1 | 3/2011 | Sirleaf |
| 2012/0089518 | A1 | 4/2012 | Blonchek |
| 2012/0284056 | A1 | 11/2012 | Hofstetter |
| 2013/0054271 | A1 | 2/2013 | Langford et al. |
| 2013/0124855 | A1 * | 5/2013 | Varadarajan ............ G06F 21/31 |
| | | | 713/155 |
| 2013/0218594 | A1 | 8/2013 | Skocic |
| 2014/0039929 | A1 | 2/2014 | Vdovjak et al. |
| 2014/0164022 | A1 * | 6/2014 | Reed ................... G06F 19/3481 |
| | | | 705/3 |
| 2014/0245396 | A1 * | 8/2014 | Oberheide ............ H04W 12/06 |
| | | | 726/4 |
| 2015/0073827 | A1 | 3/2015 | Crapo et al. |
| 2015/0074409 | A1 * | 3/2015 | Reid ..................... H04L 63/061 |
| | | | 713/171 |
| 2015/0149208 | A1 | 5/2015 | Lynch et al. |
| 2015/0278462 | A1 | 10/2015 | Smoley et al. |
| 2016/0110523 | A1 * | 4/2016 | Francois ................ G06Q 50/24 |
| | | | 705/2 |

FOREIGN PATENT DOCUMENTS

| | | | | |
|---|---|---|---|---|
| WO | WO-2012104771 | A2 * | 8/2012 | ............. G06F 21/10 |
| WO | 2014206795 | A1 | 12/2014 | |
| WO | WO-2014206795 | A1 * | 12/2014 | ......... G06F 21/6245 |
| WO | WO-2015036935 | A1 * | 3/2015 | |
| WO | 2015043744 | A1 | 4/2015 | |

OTHER PUBLICATIONS

International Search Report and Written Opinion for International Application No. PCT/US2016/051791, dated Nov. 9, 2016, 12 pages.

Abukhousa et al., "e-Health Cloud: Opportunities and Challenges," Future Internet, vol. 4, 2012, pp. 621-645.

Fletcher et al., "Development of Mobile-Based Hand Vein Biometrics for Global Health Patient Identification," Global Humanitarian Technology Conference (GHTC), 2014 IEEE. 7 pages.

LifeMed ID SecureReg ID End User Training Manual, believed to be publicly available more than one year prior to the filing date of the instant application, 25 pages.

LifeMed ID SecureReg Product Features, believed to be publicly available more than one year prior to the filing date of the instant application, 2 pages.

"Positive patient identification: Why patient identifiers matter," Imprivata, Retrieved online from https://web.archive.org/web/20160811143129/https://www.imprivata.com/patient-identification, Aug. 11, 2016, 11 pages.

Rightpatient, Retrieved online from https://web.archive.org/web/20160718083138/http://www.rightpatient.com/rightpatient-biometric-patient-safety-system/, Jul. 18, 2016, 3 pages.

Schoenberg et al., "Internet based repository of medical records that retains patient confidentiality," British Medical Journal, vol. 321, Nov. 11, 2000, pp. 1199-1203.

Wu et al., "Secure Sharing of Electronic Health Records in Clouds," 2012 8th International Conference on Collaborative Computing: Networking, Applications and Worksharing (ColaborateCom), IEEE, 2012, 8 pages.

* cited by examiner

PATIENT IDENTIFICATION SYSTEMS AND METHODS

RELATED APPLICATIONS

This application claims priority to U.S. Provisional Patent Application No. 62/266,277, filed Dec. 11, 2015, the entire contents of which are incorporated herein by reference.

BACKGROUND

Patient intake and information management systems present in use are inefficient and error-prone. Primarily conducted via paper based forms, such systems have not improved in process or quality since their initial conception. It relies upon the patient manually filling out forms and actually being who they claim to be and not using someone else's identify in order to secure healthcare services, and subsequent data entry of manually-filled in forms. Further, there is limited system and methods in place at the point of registration to ensure non-fraudulent, accurate and complete data capture. Photocopying or scanning images of the patient's identifying information (e.g., driver's license and insurance card) and placing it in a patient file are the tools presently being used. Biometric data-based authentication and smartcards has also recently been introduced into the process. However, such tools may not assist with patient intake. Further, smartcards are "static" authenticators, and may be less secure.

Conventional patient intake systems collect patient demographic and health data and store them into an electronic medical record (EMR, sometimes referred to as electronic health record, or EHR). Each healthcare entity (e.g., a hospital) may have patient EMR stored in their electronic medical record system (EMR system). Typically, a healthcare entity may not access the EMR system of another healthcare entity. While many healthcare entities allow the patient to view their EMR, there is limited means by which the patient may update their record, or provide their own healthcare data (e.g., blood pressure tests, weight, activity levels) and the like. Many healthcare entities (e.g., a hospital a network of hospitals) have established a mobile experience that allows the patient to login and view their record through a patient portal. However, such systems do not permit the patient to modify data, or provide a more secure way to authenticate a patient.

SUMMARY

In general, this disclosure is directed to a patient information management system for matching a patient with their health records. The patient information management system, according to some exemplary embodiments can include a cloud-based application server, comprising a database having patient demographic records stored thereon. The cloud-based application server can be configured to retrieve, over a network, electronic medical records (EMRs) from one or more electronic medical record systems (EMR systems) to a corresponding patient demographic record stored in the database.

In some examples, a client application interface can be provided on a client computing device to communicate with the cloud-based application server. Further, a mobile security token can be provided on a patient computing device to communicate with the cloud-based application server. The cloud-based application server can be configured to send the one or more authenticators to the client computing device, and in response to the mobile security token reading the one or more authenticators, match the mobile security token with the patient's demographic record in the database, and thereby authenticate a patient.

A method of accessing a patient's information from multiple electronic medical record (EMR) systems, according to some examples can involve providing a patient information management system according to some embodiments. The method can include the step of sending, from the cloud-based application server, one or more authenticators to the client computing device. The method can involve using the mobile security token to read the one or more authenticators sent to the client computing device. Further, the mobile security token can be matched to a patient demographic record in the database to authenticate the patient using the linked mobile security token prior to accessing and/or releasing the patient's record from an EMR system.

An exemplary method of linking a patient's demographic data stored on a cloud-based application server to an EMR system of a client healthcare entity can include generating, from the cloud-based application server, an authenticator, and sending the authenticator to the client computing device located at the client healthcare entity. The method can further include generating a single-use QR code based on the authenticator, and displaying the single-use QR code using the client computing device. The single-use QR code can be read using the mobile security token. An automated matching exercise can be performed to determine if another record exists in the cloud-based application server or another EMR system in communication therewith, that matches patient data captured from at least one of the client computing device or the patient computing device. Finally, the mobile security token can be linked to a patient record created and stored in the cloud-based application server.

The details of one or more examples are set forth in the accompanying drawings and the description below. Other features, objects, and advantages will be apparent from the description and drawings, and from the claims.

DETAILED DESCRIPTION

Figure 1:
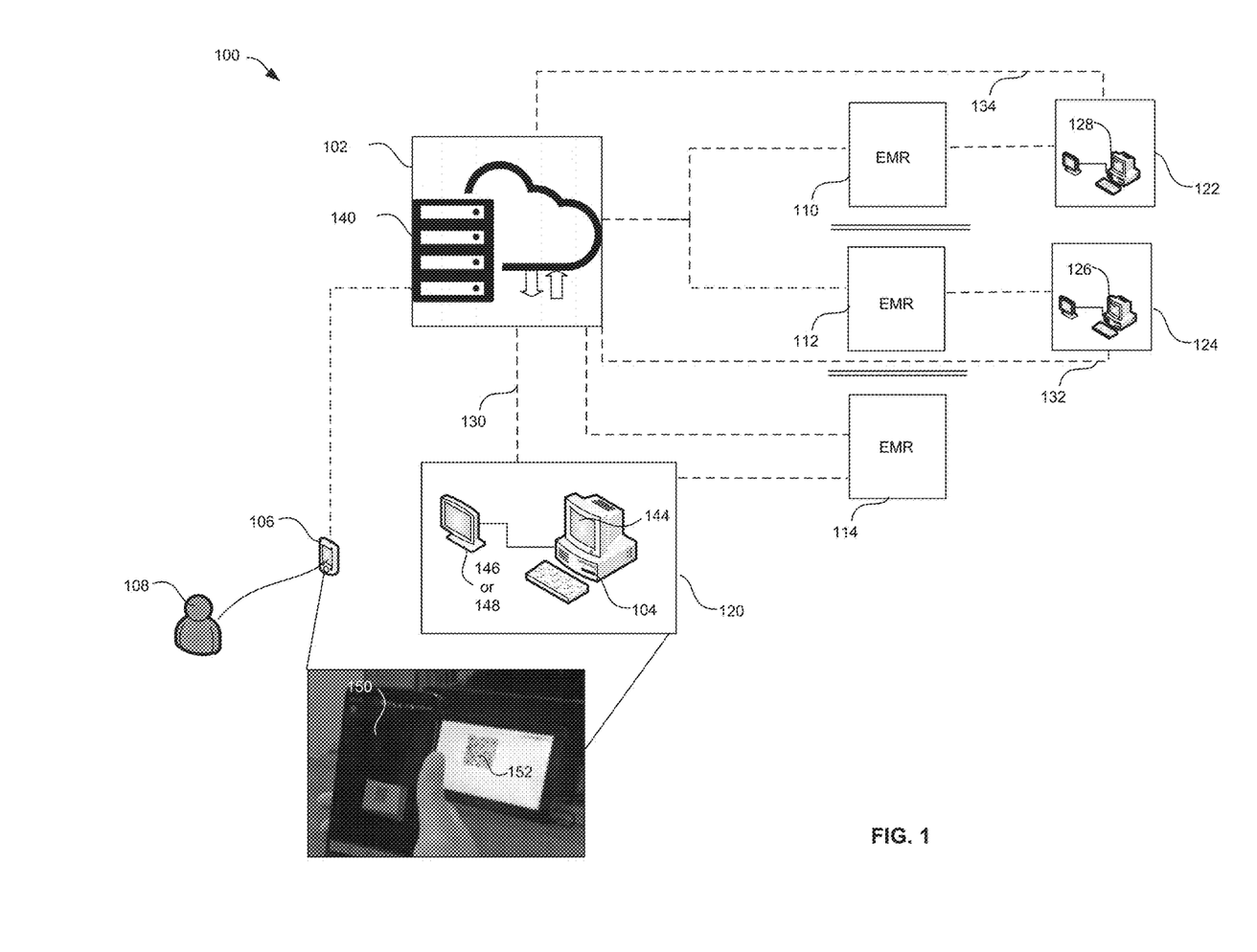
FIG. 1 is a network schematic of a patient information management system according to an exemplary embodiment.

FIG. 1 shows a high-level schematic of certain embodiments of a patient identification system 100. Such systems can facilitate initial patient 108 registration (hereinafter, "patient intake") at a healthcare entity (a hospital, clinic, healthcare provider, or a network of such hospital, clinics, and/or healthcare providers). Such systems can also facilitate authenticating the patient 108 during subsequent visits. Such embodiments permit accurately identifying a patient 108 (to prevent issues with misidentification of a patient for another person), and retrieve records corresponding to that patient 108. Such embodiments also reduce errors such as inadvertent access or modification of another patient record. Systems and methods provided herein may also allow the patient 108 to modify or update his or her own electronic record with insurance details, demographic data or even patient 108-generated clinical information (blood pressure readings, FitBit results, updated prescription list, etc.).

Continuing with FIG. 1, the patient 108 information management system comprises a cloud-based application server 102. The cloud-based application server 102 can host and process one or more cloud-based applications (hereinafter "apps"). The apps may run on remote computing devices such as computing devices provided at a healthcare entity's facility (hereinafter "client computing device 104") or a patient computing device 106 physically possessed by a patient 108. It should be understood that the term cloud-based application server, as used herein includes any network server remotely located from the healthcare entity. As such, a deployed server capable of being offline and permitting selective and/or restricted access to a healthcare entity is also contemplated within the scope of the present disclosure.

Continuing with the architecture provided in FIG. 1, the cloud-based application server 102 may be accessed by one or more healthcare entities' EMR systems 110, 112, 114 provided on computing devices over a network. In FIG. 1, one such client healthcare entity 120 in communication with its associated EMR system 114 is shown enlarged in the lower left portion and is described in detail further below. Each of the other EMR systems 110, 112, can also be associated with its own client healthcare entity 122, 124, each having its own client computing device 126, 128. Each client healthcare entity 120, 122, 124, and associated client computing devices 104, 126, 128 can further be in communication with the cloud-based application interface (e.g., over respective networks 130, 132, 134). As used herein, a client healthcare entity can be a hospital, with various services such as clinics, labs, rehabilitation centers, diagnostic facilities associated therewith.

The network connections 130, 132, 134 illustrated in dashed lines in FIG. 1 between the client computing devices 104, 126, 128 and the cloud-based application server 102 represent any type of communications, such as over the internet or via a cellular device network. Further, the network connections can be secure, such as a virtual private network (VPN), or may require credentials from the client computing device 104 so as to securely transmit data therebetween. As mentioned previously, each client computing device 104, 126, 128 (related to a client healthcare entity 120, 122, 124) is not connected to other client healthcare entities as indicated by the double horizontal line therebetween, and can therefore not access EMR systems of any healthcare entity other than its own EMR system.

With continued reference to FIG. 1, the cloud-based application server 102 comprises a database 140. The database 140 can have patient 108 demographic records stored thereon. As used herein, the term demographic data may include a patient's identifying information (e.g., name, address, medical record number (MRN), social security number and the like). At least one of the identifying data can be unique to the patient 108. Optionally, the database 140 may not store any medical data thereon, but may be in communication with EMR systems over a network. The cloud-based application server 102 can have software, such as database 140 management systems, for interacting with the EMR systems and/or patient 108 computing devices.

In one example, each EMR system may have a corresponding medical record number (MRN) for every patient 108, and the database 140 can store a set of MRNs associated with various EMR systems for each patient 108. The database 140 may not store any medical data thereon, but patient 108 demographic data on the database 140 may be linked (e.g., via a MRN) to medical data in an EMR stored on an EMR system. Thus, the cloud-based application server 102 can retrieve, over the network, an EMR of a corresponding patient 108 demographic record (stored in the database 140), and send, over the network, the retrieved EMR to either a client computing device 104 or a patient computing device 106. The database 140 can also be queried by at least one of a patient computing device 106 or a client computing device 104 over a network to retrieve EMR or other data.

Shifting attention to the lower left portion of FIG. 1, an enlarged view of a single client healthcare entity 120 is illustrated. Certain components of the client healthcare entity, such as the client computing device 104 may not be physically a part of the patient 108 information management system. However, the patient 108 information management system includes a client application interface 144 provided on the client computing device 104. The client application interface 144 can be a software program installed on the client computing device 104's memory. The client application interface 144 can use hardware (e.g., network cards) provided on the client computing device 104 (or peripherals connected thereto) to communicate with the cloud-based application server 102 over a network (such as internet or cellular network), optionally using a virtual private network or other credentials to facilitate a secure connection. For instance, the client computing device 104 can be a computer or a set of computers provided on a local area network and physically located at the client healthcare entity and linked to the cloud-based application server 102 over a VPN connection. Further, the client computing device 104 can also be connected to a point-of-sale (POS) device 146, configured for accepting electronic payment (e.g., using a credit card) and/or the patient's signature. Alternatively, instead of a POS device 146, the client computing device 104 can include a patient-facing display screen 148 to authenticate the patient 108, as will be explained further below.

As is apparent to one skilled in the art, EMR systems other than the EMR system associated with a particular client healthcare entity may not be accessible by the client computing device 104. In FIG. 1, this is illustrated by the double horizontal line between each healthcare entity. However, if a patient 108 is authenticated by the client healthcare facility EMR from the healthcare entity's own EMR system can be retrieved through the cloud-based application server 102, as will be explained further below.

Referring again to FIG. 1, the patient 108 information management system further comprises a mobile security token 150 provided on a patient computing device 106. As seen in FIG. 1, the mobile security token 150 is separate and distinct from the client application interface 144 provided on the client computing device 104. Thus, the patient 108 information management systems according to certain embodiments of the present disclosure can have two distinct and/or independent communication pathways for each client healthcare entity: a first communication pathway comprising network connection between the client application interface 144 and the cloud-based application server 102, and a second communication pathway between the patient computing device and the cloud-based application server 102. The first and second communication pathways can be independent of each other.

In some embodiments, the patient computing device 106 (e.g., smartphone, tablet or a mobile personal computer) is "tokenized" by an app. Once tokenized, the mobile security token 150 is "mobile" in the sense that a patient 108 may carry it with them, rather than having it at a fixed location. As is recognized by one skilled in the art, such mobile security tokens have distinct advantages over known physical tokens. Unlike a physical token (such as a smartcard or biometric modalities) a mobile security token 150 has the ability to operate in two environments: when the patient 108 is physically present at the client healthcare facility and when the patient 108 is remote but would like to view or update their record or check-in to receive telehealth services. The mobile security token 150 may be used to the authenticate the patient, in conjunction with a second "factor" authentication, such as a passcode. Further, the patient's physical presence is verified by a one-time code that verifies that the patient is present at the physical location of a client healthcare entity, and at a given time. This may involve the use of the first communication pathway between the client application interface 144 on the client computing device 104 and the cloud-based application server, as well as the second communication pathway between the cloud-based application server and the client computing device.

The mobile security token is unique to each patient 108. For instance, the cloud-based application server may generate a unique identifier corresponding to the patient computing device, and place it in and/or as the mobile security token in the patient computing device's memory. The unique identifiers within/corresponding to each mobile security token 150 may be indexed in the patient's demographic record in the database 140. Thus, the cloud-based application server 102 when interacting with the patient computing device (e.g., over the second communication pathway) would be able to recognize the patient computing device as having the unique mobile security token 150 and thereby authenticate the patient 108.

The cloud-based application server 102 can send a one-time verification code to the client computing device 104 over the first communication pathway, and in response to the patient computing device reading the one time verification code (e.g., sent over the second communication pathway), verify that the patient having a patient computing device storing the unique mobile security token 150 is physically present at the client healthcare entity at that instant. This process would verify that the patient is who they claim to be. The patient computing device can communicate with the cloud-based application server 102 and/or the client application interface 144 provided on the client computing device 104 to read the one-time verification code from the client computing device 104. Such systems and methods can be used to provide a multifactor authentication that is more secure relative to existing authentication systems.

In some embodiments, the cloud-based application server 102 can require two-factor authentication to authenticate a patient 108. At least one of the two authenticators can be the mobile security token placed by the cloud-based application server in the patient computing device's memory, while the other authenticator can be a patient 108—selected encryption key, such as a numeric code, an image, a word or a phrase, or biometric authenticators (e.g., fingerprint, voice print, retinal scan, and the like). In addition, the cloud-based application server 102 can send a one-time location verification code to the client computing device 104, which can be a numeric code corresponding to the date and time. The numeric code can be optionally encoded into a machine-readable code which can be read near-field, such as a QR code, and displayed to the patient 108. The patient 108 may use the patient computing device to scan the machine readable code, which would then be sent over a network to the cloud-based application interface. In this example, the machine-readable code 152 is generated at the client computing device 104. Alternatively, the machine-readable code 152 can be generated by the cloud-based application server 102.

Figure 2:
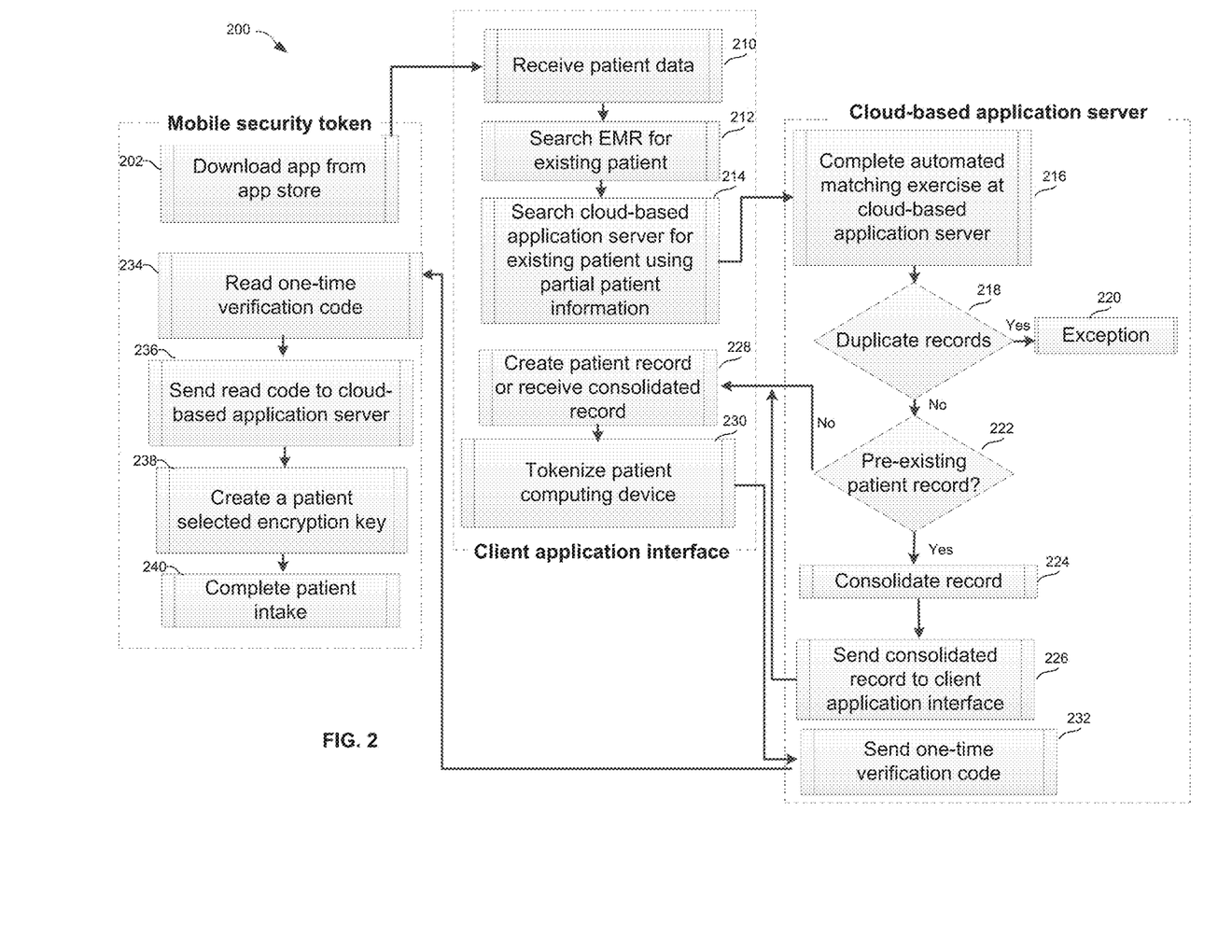
FIG. 2 is a flowchart illustrating an exemplary method of patient intake using the patient information management system of FIG. 1.

FIG. 2 is a flowchart illustrating a method 200 of initial patient intake at a client healthcare facility. The initial patient intake can be used to establish a patient's mobile security token 150 and link it with a patient's demographic record in the cloud-based application server 102. The mobile security token 150 can be unique to the patient 108, and can be used to authenticate the patient 108 during future visits at the same healthcare facility. Further, the mobile security token 150 and linked demographic data can also be used to consolidate patient records on multiple EMR systems.

In the example illustrated in FIG. 2, the patient 108 uses a patient computing device 106, such as a smartphone to establish the mobile security token 150. At step 202, the patient 108 may go to an app store and use existing credentials (e.g., an Apple ID or a Google account) to download an app.

In some embodiments, some of the patient 108 data may be pre-populated at the time of, or before patient intake. For instance, a healthcare entity, such as a healthcare provider or payer may populate or update the cloud-based application server 102 with a patient record. In such an embodiment, healthcare providers may supply patient 108 data contained in their record system. Data in the provider or payer's record may come from a trusted third party source (e.g., patient's employer). Providers and payers may elect to use this information from the patient 108 to update their own records or continue to operate with their existing workflows that support demographic updates. For example, some payers may not accept updates to a member's demographic details except when it comes directly from the member's employer during an enrollment transaction (e.g., open enrollment period).

In another example, the patient 108 may pre-populate their own record where none exists within the client application interface 144. The patient 108 would establish their record through their mobile security token 150, and link their mobile security token 150 to the cloud-based application interface as will be described further below. Such embodiments allow the patient 108 to submit updates to their own record and allow other stakeholders (e.g., payer, provider) to have access to patient 108 data.

The patient 108 may then proceed to a client healthcare entity's physical location, whereby patient intake is completed. For instance, the patient's identifying information (e.g., government-issued ID, social security number, name, address, etc.) is collected at step 210 and sent to the client application interface 144. One or more of the identifying information can be used to locate an existing patient record within the client healthcare entity's EMR system by initiating a search at step 212 and/or demographic data within the database 140 of the cloud-based application server 102. This may involve querying the database 140 at step 214 to access at least one field of a patient 108 demographic record, and using the at least one field of the patient 108 demographic record to access the patient's EMR corresponding to the patient 108 demographic record. For instance, the patient 108 can be identified based on a corresponding Medical Record Number ("MRN") in the client healthcare entity's EMR system and/or the database 140 of the cloud-based application server 102.

Figure 3:
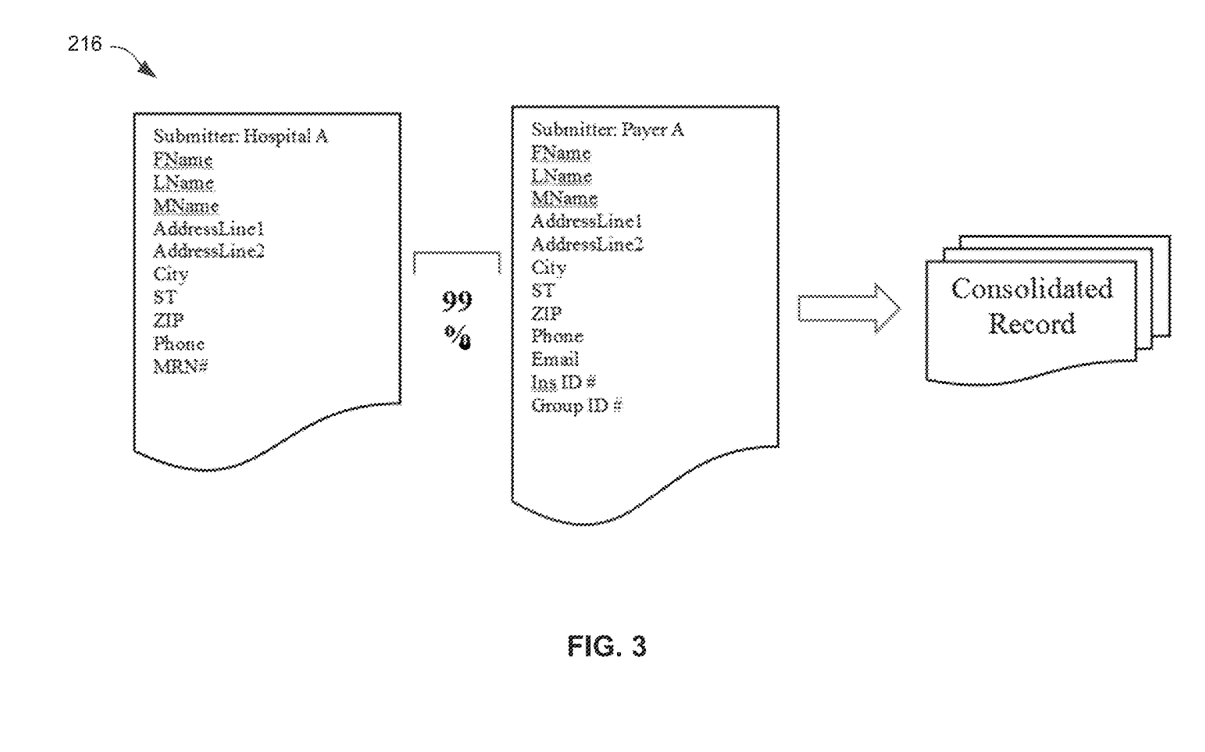
FIG. 3 is an illustration of an automated patient matching exercise according to an exemplary embodiment.

Continuing with FIG. 2, in step 216, using the cloud-based application server 102, an automated matching exercise can be performed to determine if another record exists in the cloud-based application server 102 or the healthcare entity's EMR system in communication with the client computing device 104, that matches patient 108 data captured during initial intake (e.g., at step 210). During the automated matching exercise, the cloud-based application server 102 would determine, at step 218 if duplicate records exist within the load file submitted by the plan. If duplicate records exist, the cloud-based application server 102 will generate an exception at step 220. The cloud-based application server 102 would then determine, at step 222, if any of the records within the client application interface 144 match above a minimum threshold of probability to another record previously established by another entity. FIG. 3 illustrates one such automatic matching exercise. Returning to FIG. 2, if matches to pre-existing records are found, at step 224, cloud-based application server 102 may align or augment the pre-existing record with data that are available (e.g., from another provider or a payer), creating one consolidated record with attributes provided by multiple entities (e.g., provider, payer, healthcare entity). Once the patient 108 is identified, demographic data, and data from other probabilistic fields in the database 140 can be linked to the client application interface 144 at steps 226, and 228.

If a pre-existing patient record is found, the consolidated patient record is presented. Otherwise, a patient record is created. At step 230, the patient computing device is "tokenized" to place a mobile identity token therein, and associate the mobile security token with the patient record within the client application interface 144, while the patient record is associated with a corresponding MRN in the client healthcare facility's EMR system. At step 230, the client application interface requests a one-time verification code, which is sent by the cloud-based application server at step 232. The one-time verification code is read by the patient computing device at step 234, and is sent to the cloud-based application server at step 236. The cloud-based application server confirms that the patient is physically at the same location as the client computing device, and is transmitting the one-time verification code from the same device on which the mobile security token is placed. As such, completion of the loop (one-time verification code sent from the cloud-based application server to the client computing device, and again, sent from the patient computing device to the cloud-based application server) step "tokenizes" the patient computing device, which constitutes the first authentication factor.

A second authentication factor can be selected at step 238 to enhance security. The second authentication factor can be a patient selected encryption key, such as a PIN, a password, a phrase, an image, or biometric data. The second authentication factor is then associated with the patient record. Once associated, patient intake is completed at step 240.

The patient 108 data is then displayed to the patient 108 (e.g., using a patient 108-facing display or a POS device 146).

Once the intake is complete, at step 240, the client application interface 144 requests to the cloud-based application interface, the associated patient record from the EMR system using an HTML web service to call. The cloud-based application server 102 sends an HL7 message to the corresponding EMR system, whereby the corresponding MRN is sent to the EMR system's search functionality. The EMR system pushes the patient's EMR to the client application interface 144 either directly through a separate network or indirectly (e.g., through the cloud-based application server 102). For instance, the client application interface 144 may display the EMR system on the client computing device 104. Alternatively, the client application interface 144 may open a separate software program which acts as a portal to the EMR system, whereby the patient's EMR can be seen.

Optionally, at the end of creating or consolidating patient 108 data, the patient's picture can be taken, either via a camera in communication with the client application interface 144, or by pulling a photo from the patient's government-issued ID. At the end of the patient intake, at step 238, the patient's picture and demographic data are linked to the patient's mobile security token 150. Data linked at the end of patient intake to establish a new record and/or consolidate an existing record include items such as medical record number (MRN), patient 108 name (first, last, middle, prefix, suffix), patient 108 address (home or primary), gender, date of birth, insurance coverage (insurance name, insurance ID number, and group number), phone number(s), the account number by which the patient 108 is known to the payer, email address, and social security number.

As discussed above, methods such as those illustrated in FIG. 2 facilitate two-factor authentication. In such cases, at least one factor can be the mobile security token generated and linked to the patient computing device during initial patient intake, and the second factor can be the patient-selected encryption key. The patient 108 physically appears at the client healthcare facility, uses their patient computing device to read a one-time machine readable verification code, and transmit the read data back to the cloud-based application server 102. This step would confirm that the patient is physically present client healthcare facility at the time of the one-time verification code being sent. Further, this step would confirm that the patient is sending confirmation that the one-time verification code is read from the same patient computing device that is linked to their mobile security token. As the mobile security token 150 is previously linked to the patient computing device, the reading of the one-time verification code requested by the client application interface 144 authenticates the patient 108. A second factor can be added to improve security. For instance, at the time of intake, the patient 108 can select an encryption key, such as a numeric code, an image, a word or a phrase, or biometric authenticators (e.g., fingerprint, voice print, retinal scan, and the like). Once the first-step of the authentication is completed, the cloud-based application server 102 can communicate with at least one of the client application interface 144 or patient computing device to prompt the patient 108 to enter their patient 108-selected encryption key (e.g., enter a PIN, password or phrase, select a picture from a set of different pictures, enter a biometric authenticator) and the like. As will be discussed below, the linked mobile security token 150, and the patient-selected encryption key can both be used to authenticate a patient 108 during future visits.

Figure 4:
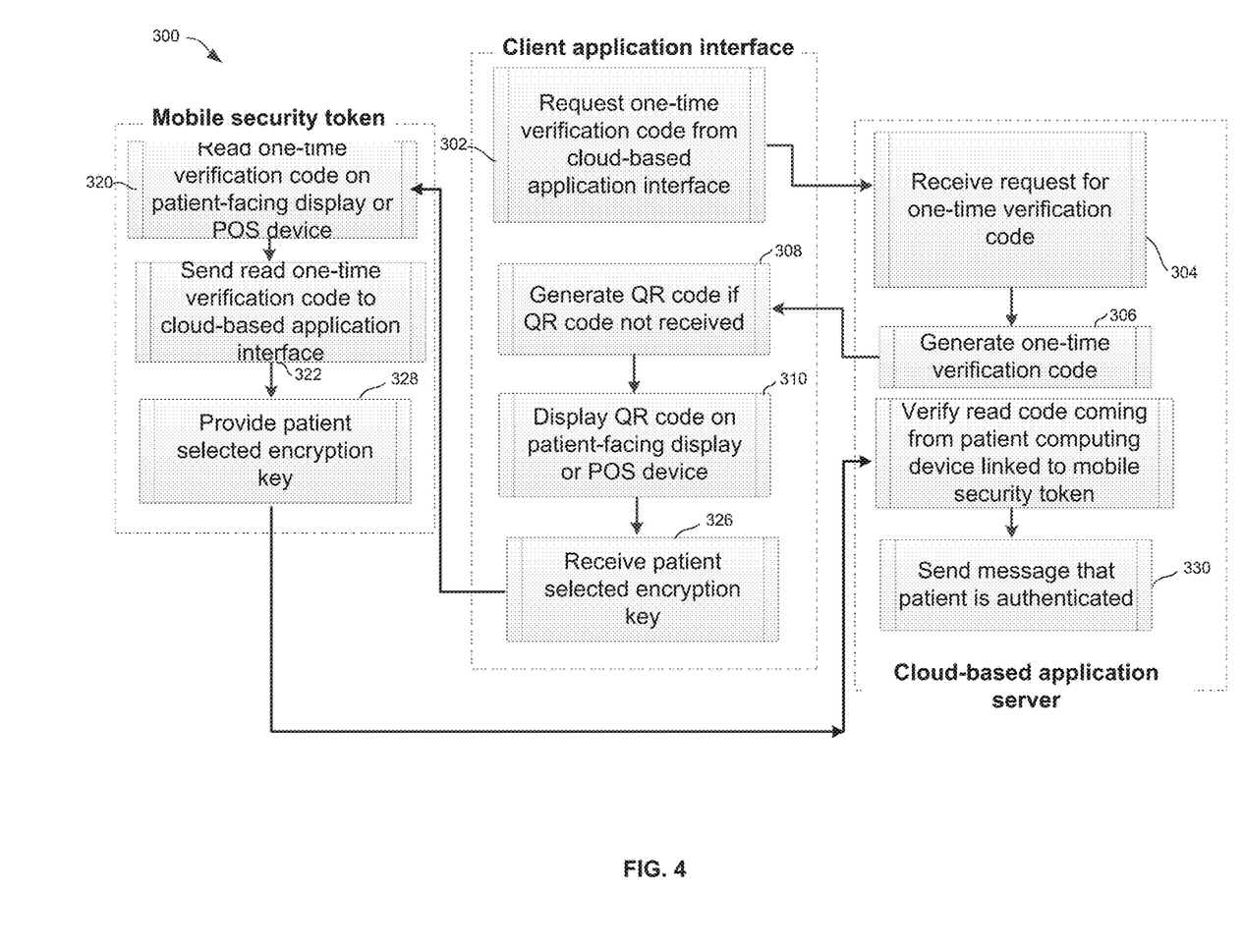
FIG. 4 is a flowchart illustrating an exemplary method of authenticating a patient using the patient information management system of FIG. 1.

FIG. 4 illustrates a method 300 of authenticating a patient 108 when visiting a client healthcare entity. The client application interface 144 initiates patient authentication at step 302 by requesting the cloud-based application interface to send a one-time verification code. Upon receiving the request at step 304, the one-time verification code is generated and sent from the cloud-based application server 102 to the client application interface 144 over the first communication pathway at step 306. In the case of telehealth providers, one or more authenticators could instead be sent by secure email to the patient 108.

The one-time verification code can be a machine-readable code having encoded data that can be read by a machine. In some examples, the machine-readable code is a visible barcode. In certain embodiments, the machine-readable code is a two-dimensional barcode, such as a QR code. Alternatively, the machine-readable code can be a magstripe, chipped cards, and the like. The machine-readable code can be generated by the client application interface 144 at step 308 using and incorporating code data received from the cloud-based application server 102. In other embodiments, the QR code, that incorporates the code data, may be generated directly by the cloud-based application server 102. In either case, the QR code may then be displayed, at step 310 on a device connected to the client computing device 104. For instance, the client computing device 104 can include a patient-facing display screen 148, or a POS device 146, which can display the QR code. The QR code, unlike conventional QR codes may not be "static." This one-time QR code may incorporate code data that includes a device ID, a workstation ID, and/or a location ID and a time stamp. For instance, a different QR code or code data (e.g., a QR code with different code data) can be sent to the client computing device 104 each time the patient 108 is to be validated. Further, the QR code can automatically expire shortly after being requested by the client application interface 144. For instance, the cloud-based application server 102 can automatically stop accepting the QR code sent to the client computing device 104 as a valid one-time verification code after a predetermined interval of time (e.g., 10 minutes). Thus, the one-time verification code generated by the cloud-based application server 102 is dynamic that changes for each authentication request at a healthcare facility based on the computer terminal or kiosk at which the patient appears, and/or expires automatically after a predetermined interval of time.

Returning to FIG. 3, the method 300 comprises the step 320 of using the patient computing device to read or respond to the one-time verification code sent to the client computing device 104. This may involve, in an example illustrated in FIG. 1, pointing a patient computing device 106, such as a smartphone toward the client computing device 104 (or a patient 108-facing display or POS device 146). Referring again to FIG. 3, an app in communication with the mobile security token 150 can communicate with the camera of the patient's smartphone, and scan the machine-readable code (e.g., QR) displayed on the client computing device 104 (patient 108-facing display or POS device 146). The read QR code can be sent to the cloud-based application interface at step 322. The location/device/terminal ID of the client healthcare facility and the time and date of visit can be encoded into the machine-readable code, such that the cloud-based application server confirms that the patient is physically at the client healthcare facility at the same location as the client computing device and/or terminal and/or kiosk to which the machine-readable code was sent. Further, the cloud-based application server confirms (e.g., at step 330) that the read data is received from the patient computing device linked to the mobile security token unique to that patient. The method can further include performing a second factor authentication to authenticate the patient 108 at steps 326 and 328. In some examples, the second factor authentication includes entering a patient 108-selected encryption key on to the client computing device 104.

The method further comprises the step of matching the mobile security token 150 to a patient 108 demographic record in the database 140, and thereby authenticating the patient 108 using the linked mobile security token 150 prior to accessing and/or releasing the patient's EMR from an EMR system corresponding to the client healthcare entity.

Once authenticated, the cloud-based application server 102 can send verification at step that the patient 108 has been successfully authenticated. The client application interface 144 can then retrieve a corresponding EMR for the patient 108. This may involve querying the database 140 to access at least one field of a patient 108 demographic record, after the patient 108 is authenticated. At least one field of the patient 108 demographic record can then be used to access the patient's EMR corresponding to the patient 108 demographic record linked to the mobile security token 150. For instance, the database 140 can be queried using patient 108 demographic record, or unique identifiers of the mobile security token 150, following which, using a MRN stored in the database 140 for the patient 108, an EMR can be retrieved. The retrieved EMR can be displayed to the patient 108 (e.g., using a patient 108-facing display or POS device 146). Displayed data can include the patient's demographic data (e.g., patient 108 picture, name, address, date of birth, insurance details, and any additional data as appropriate) to allow the patient 108 to confirm their medical data.

In some embodiments, a patient 108 could update an existing record. The patient 108 could use their mobile security token 150 and one or more authenticators received from the cloud-based application interface to allow them access to their record. Upon accessing their record, the patient 108 could update or view their details from the patient computing device 106. In such cases, the uniqueness of the mobile security token 150 allows a patient 108 to edit their own data, but also reduces the potential for a patient 108 inadvertently accessing their record. The mobile security token 150 thus acts as a trusted pointed of exchange, assuring the provider of the authenticity of data coming from the patient computing device 106.

In some embodiments, if insurance details are updated at a healthcare provider (a new ID# and Group # for example) and the patient 108 visited another location within the client healthcare entity (e.g., a clinic, a lab or a diagnostic facility within the same hospital), the updated insurance details would immediately carry forward from one EMR to the next or from the EMR to a payment management system. The patient 108 may not be required to complete registration paperwork, thereby reducing the need for manual data entry. Such embodiments facilitate using the client healthcare entity's integration with the cloud-based application server 102 as a "hub" for the latest and most trusted demographic and insurance details.

Example system and methods described herein provide one or more technical solutions. By providing two distinct pathways for communication (one between the cloud-based application server and the patient computing device, and a second pathway between the cloud-based application server and the client application interface), patient authentication is more secure relative to traditional security token based systems because multiple modes of authentication. Further, dynamic machine-readable codes and multi-factor authentication described herein also enhances security. Such systems also provide the ability for the patient or a trusted third party to securely enter or modify data, and reduce errors or inadvertent access of another patient's medical records.

Various examples have been described. These and other examples are within the scope of the following claims.

What is claimed is:

1. A patient information management system for matching a patient with their health records, comprising:
   a cloud-based application server, comprising a database having patient demographic records stored thereon, the patient demographic records being linked to one or more electronic medical records (EMRs) on a healthcare entity's electronic medical record system (EMR system), the cloud-based application server configured to retrieve, over a network, EMRs from one or more EMR systems to a corresponding patient demographic record stored in the database;
   a client application interface provided on a healthcare entity computing device, the client application interface being configured to communicate with the cloud-based application server, the healthcare entity computing device being physically located at a client healthcare entity such that EMR systems, other than the EMR systems of the client healthcare entity, being inaccessible by healthcare entity computing device; and
   a mobile security token generated by the cloud-based application server and provided on a patient computing device separate and distinct from the healthcare entity computing device, the mobile security token being configured to communicate with the cloud-based application server, wherein the mobile security token is unique for each patient in the one or more EMRs, whereby, the cloud-based application server is configured to:
   link the patient computing device to the mobile security token in the patient demographic record,
   in response to receiving a request for patient authentication for a particular patient from the healthcare entity computing device, generate a one-time verification code for the particular patient, wherein the one-time verification code comprises a dynamic code that changes for each request at the healthcare entity computing device,
   send the one-time verification code generated by the cloud-based application server to the healthcare entity computing device,
   receive an indication of the one-time verification code and an indication of the mobile security token from the patient computing device, and
   in response to receiving the indication of the one-time verification code and the indication of the mobile security token from the patient computing device, determine that the one-time verification code matches the generated one-time verification code and that the mobile security token matches an expected mobile security token stored in the patient demographic record, and thereby authenticate the particular patient.

2. The patient information management system of claim 1, wherein, when the patient is authenticated, the cloud-based application service is further configured to:
   access the patient's EMR stored on a healthcare entity's EMR system, and
   release the EMR to at least one of the client application interface or the patient computing device.

3. The patient information management system of claim 1, wherein the cloud-based application server is further configured to require two authenticators to authenticate a patient.

4. The patient information management system of claim 3, wherein at least one of the two authenticators is the mobile security token.

5. The patient information management system of claim 1, wherein the healthcare entity computing device includes a Point-of-Sale (POS) device configured to accept payment from the patient for the healthcare services.

6. The patient information management system of claim 5, wherein the patient computing device is a smartphone configured to read the one-time verification code generated by the cloud-based application server to the healthcare entity computing device.

7. The patient information management system of claim 5, wherein the mobile security token corresponds to a unique identifier for each patient.

8. A method of accessing a patient's information from multiple electronic medical record (EMR) systems, comprising:
   providing a patient information management system, comprising:
      a cloud-based application server, comprising a database having patient demographic records stored thereon, the cloud-based application server being connected to one or more electronic medical record systems (EMR systems) over a network, each EMR system being inaccessible by other EMR systems,
      a client application interface provided on a healthcare entity computing device physically located at a healthcare entity, and
      a mobile security token generated by the cloud-based application server and provided on a patient computing device separate and distinct from the healthcare entity computing device, wherein the mobile security token is unique for each patient in the one or more EMRs;
   in response to receiving a request for patient authentication for a particular patient from the healthcare entity computing device, generating, by the cloud-based application server, a one-time verification code for the particular patient, wherein the one-time verification code comprises a dynamic code that changes for each request at the healthcare entity computing device;
   sending, from the cloud-based application server, the one-time verification code generated by the cloud-based application server to the healthcare entity computing device;
   using the patient computing device to read the one-time verification code sent to the healthcare entity computing device;
   receiving, by the cloud-based application server and from the patient computing device, an indication of the one-time verification code and an indication of the mobile security token;
   determining that the one-time verification code matches the generated one-time verification code and that the mobile security token matches an expected mobile security token stored in the patient demographic record; and
   authenticating the patient using the linked mobile security token prior to accessing and/or releasing the patient's EMR from an EMR system.

9. The method of claim 8, further comprising, querying the database to access at least one field of a patient demographic record, after the patient is validated.

10. The method of claim 9, further comprising, using the at least one field of the patient demographic record to access the patient's EMR corresponding to the patient demographic record linked to the mobile security token.

11. The method of claim 10, wherein the at least one field is a medical record number (MRN).

12. The method of claim 9, wherein, at the one-time verification code sent from the cloud-based application server to the healthcare entity computing device is used to generate a QR code, the QR code comprising encoded data, the encoded data comprising physical location of the healthcare entity computing device and/or time of patient visit.

13. The method of claim 12, further comprising, reading the QR code displayed on the healthcare entity computing device using the mobile security token.

14. The method of claim 13, further comprising, sending a different QR code to the healthcare entity computing device each time the patient is to be authenticated.

15. The method of claim 12, further comprising, automatically stop accepting the QR code sent to the healthcare entity computing device as a valid one-time verification code after a predetermined interval of time.

16. The method of claim 12, further comprising, performing a second factor authentication to authenticate the patient, wherein the second factor authentication includes entering a patient-selected encryption key on to the healthcare entity computing device.

17. The method of claim 12, further comprising, establishing a first communication pathway between the patient computing device and the cloud-based application server.

18. The method of claim 17, further comprising establishing a second communication pathway between the client application interface and the cloud-based application server.

19. The method of claim 18, whereby, the first and second communication pathways are independent of each other.

20. The method of claim 18, wherein the one-time verification code is sent from the cloud-based application server to the client application interface over the second communication pathway.

21. The method of claim 20, wherein the one or more authenticators are read by the patient computing device and confirmation thereof is sent to the cloud-based application server using the first communication pathway.

22. A method of linking a patient's demographic data stored on a cloud-based application server to an Electronic Medical Record (EMR) system of a client healthcare entity, comprising:
    capturing patient demographic data;
    providing a mobile security token, generated by the cloud-based application server, on a patient computing device, wherein the mobile security token is unique for each patient in the EMR;
    in response to receiving a request for patient authentication for a particular patient from a healthcare entity computing device separate and distinct from the patient computing device, generating, from a cloud-based application server, a one-time verification code for the particular patient, wherein the one-time verification code comprises a dynamic code that changes for each request at the healthcare entity computing device;
    sending the one-time verification code generated by the cloud-based application server to the healthcare entity computing device located at the client healthcare entity, the healthcare entity computing device being in communication with the cloud-based application server;
    generating a location and/or time of visit encoded QR code based on the one-time verification code;
    displaying the QR code using the healthcare entity computing device;
    using the patient computing device to read the single-use QR code and to send the one-time verification code and the mobile security token to the cloud-based server, thereby confirming that the patient is physically present at the same location as the healthcare entity computing device;
    performing, using the cloud-based application server, an automated matching exercise to determine if another record exists in the cloud-based application server or another EMR system in communication therewith, that matches patient data captured; and
    linking the mobile security token to the patient computing device and a patient record created and stored in the cloud-based application server.

23. The method of claim 22, further comprising, receiving, at the cloud-based application server, a patient-selected encryption key, and linking the patient record with the patient-selected encryption key.

24. The method of claim 23, wherein the patient-selected encryption key is received by the cloud-based application server from at least one of the healthcare entity computing device and the patient computing device.

25. The method of claim 23, wherein the patient-selected encryption key is received during a patient's initial visit to the client healthcare entity.

* * * * *